(12) United States Patent
Brannan et al.

(10) Patent No.: US 11,103,307 B2
(45) Date of Patent: Aug. 31, 2021

(54) SYSTEM AND METHOD FOR TREATING COPD AND EMPHYSEMA

(71) Applicant: Covidien LP, Mansfield, MA (US)

(72) Inventors: Joseph D. Brannan, Erie, CO (US);
Kathy E. Rooks, Aurora, CO (US);
Giordana M. Belenchia, Boulder, CO (US); Kurt R. Smith, Boulder, CO (US)

(73) Assignee: Covidien LP, Mansfield, MA (US)

( * ) Notice: Subject to any disclaimer, the term of this patent is extended or adjusted under 35 U.S.C. 154(b) by 996 days.

(21) Appl. No.: 14/981,212

(22) Filed: Dec. 28, 2015

(65) Prior Publication Data

US 2016/0184013 A1 Jun. 30, 2016

Related U.S. Application Data

(60) Provisional application No. 62/098,537, filed on Dec. 31, 2014.

(51) Int. Cl.
*A61B 18/18* (2006.01)
*A61B 34/20* (2016.01)
(Continued)

(52) U.S. Cl.
CPC .......... *A61B 18/1815* (2013.01); *A61B 18/14* (2013.01); *A61B 34/10* (2016.02); *A61B 34/20* (2016.02); *A61B 2018/00023* (2013.01); *A61B 2018/0063* (2013.01); *A61B 2018/0066* (2013.01); *A61B 2018/00404* (2013.01); *A61B 2018/00541* (2013.01); *A61B 2018/00577* (2013.01); *A61B 2018/00589* (2013.01);
(Continued)

(58) Field of Classification Search
None
See application file for complete search history.

(56) References Cited

U.S. PATENT DOCUMENTS 7,233,820 B2 6/2007 Gilboa
8,242,782 B2 8/2012 Brannan et al.
(Continued)

FOREIGN PATENT DOCUMENTS

WO 2000/010456 A1 3/2000
WO 2001/067035 A1 9/2001
(Continued)

OTHER PUBLICATIONS

U.S. Appl. No. 14/503,926, filed Oct. 1, 2014, entitled "Miniaturized Microwave Ablation Assembly," to Brannan.
(Continued)

*Primary Examiner* — Oommen Jacob
*Assistant Examiner* — Shahdeep Mohammed
(74) *Attorney, Agent, or Firm* — Carter, DeLuca & Farrell LLP

(57) ABSTRACT

A system and method enabling the receipt of image data of a patient, identification of one or more locations within the image data depicting symptoms of COPD, analyzing airways and vasculature proximate the identified locations; planning a pathway to the one or more locations, navigating an extended working channel to one of the locations, positioning a microwave ablation catheter proximate the location, and energizing the microwave ablation catheter to treat the locations depicting symptoms of COPD.

15 Claims, 13 Drawing Sheets

(51) Int. Cl.
*A61B 34/10* (2016.01)
*A61B 18/14* (2006.01)
*A61B 18/00* (2006.01)

(52) U.S. Cl.
CPC ............. *A61B 2018/00642* (2013.01); *A61B 2018/00684* (2013.01); *A61B 2018/00702* (2013.01); *A61B 2018/00797* (2013.01); *A61B 2018/00821* (2013.01); *A61B 2018/00904* (2013.01); *A61B 2018/00982* (2013.01); *A61B 2018/1861* (2013.01); *A61B 2018/1869* (2013.01); *A61B 2034/101* (2016.02); *A61B 2034/107* (2016.02); *A61B 2034/2051* (2016.02); *A61B 2218/002* (2013.01); *A61B 2218/007* (2013.01)

(56) References Cited

U.S. PATENT DOCUMENTS

| | | | |
|---|---|---|---|
| 8,382,750 | B2 | 2/2013 | Brannan |
| 8,403,924 | B2 | 3/2013 | Behnke et al. |
| 8,430,871 | B2 | 4/2013 | Brannan |
| 8,552,915 | B2 | 10/2013 | Brannan |
| 8,568,401 | B2 | 10/2013 | Brannan |
| 8,568,404 | B2 | 10/2013 | Brannan |
| 8,636,664 | B2 | 1/2014 | Brannan |
| 8,882,759 | B2 | 11/2014 | Manley et al. |
| 8,945,113 | B2 | 2/2015 | Brannan et al. |
| 8,968,290 | B2 | 3/2015 | Brannan et al. |
| 9,044,254 | B2 | 6/2015 | Ladtkow et al. |
| 9,095,359 | B2 | 8/2015 | Behnke, II et al. |
| 9,121,774 | B2 | 9/2015 | Brannan |
| 9,127,989 | B2 | 9/2015 | Brannan et al. |
| 9,151,680 | B2 | 10/2015 | Brannan |
| 9,192,426 | B2 | 11/2015 | Brannan et al. |
| 9,247,992 | B2 | 2/2016 | Ladtkow et al. |
| 9,247,993 | B2 | 2/2016 | Ladtkow et al. |
| 9,259,269 | B2 | 2/2016 | Ladtkow et al. |
| 9,277,969 | B2 | 3/2016 | Brannan et al. |
| 9,301,723 | B2 | 4/2016 | Brannan et al. |
| 2006/0254600 | A1* | 11/2006 | Danek ............... A61B 1/00085 128/898 |
| 2007/0049839 | A1* | 3/2007 | Odry ........................ A61B 5/08 600/529 |
| 2009/0196480 | A1* | 8/2009 | Nields ...................... G06T 7/33 382/132 |
| 2010/0030206 | A1 | 2/2010 | Brannan et al. |
| 2010/0166270 | A1* | 7/2010 | Wiemker .............. G06T 7/0012 382/128 |
| 2010/0331834 | A1 | 12/2010 | Peterson et al. |
| 2011/0085720 | A1 | 4/2011 | Averbuch |
| 2011/0146673 | A1 | 6/2011 | Keast et al. |
| 2011/0213353 | A1 | 9/2011 | Lee et al. |
| 2012/0201445 | A1* | 8/2012 | El-Baz .................. G06K 9/621 382/133 |
| 2012/0239024 | A1 | 9/2012 | Ladtkow et al. |
| 2012/0289815 | A1* | 11/2012 | Keast ..................... A61B 5/062 600/411 |
| 2013/0223702 | A1 | 8/2013 | Holsing et al. |
| 2014/0046174 | A1 | 2/2014 | Ladtkow et al. |
| 2014/0270441 | A1 | 9/2014 | Baker |
| 2014/0276033 | A1 | 9/2014 | Brannan et al. |
| 2014/0276739 | A1 | 9/2014 | Brannan et al. |
| 2014/0290830 | A1 | 10/2014 | Brannan |
| 2015/0238270 | A1* | 8/2015 | Raffy ..................... A61B 34/10 600/407 |
| 2016/0000302 | A1 | 1/2016 | Brown et al. |
| 2016/0038248 | A1 | 2/2016 | Bharadwaj et al. |
| 2016/0051221 | A1 | 2/2016 | Dickhans et al. |
| 2016/0051327 | A1 | 2/2016 | Brannan |

FOREIGN PATENT DOCUMENTS

| | | |
|---|---|---|
| WO | 2007/106495 A2 | 9/2007 |
| WO | 2014/070820 A2 | 5/2014 |

OTHER PUBLICATIONS

U.S. Appl. No. 14/880,338, filed Oct. 12, 2015, entitled "Computed Tomography Enhanced Fluoroscopic System, Device, and Method of Utilizing the Same," to Weingarten et al.
International Search Report and Written Opinion issued by the Japan Patent Office in corresponding International Application No. PCT/US2015/067696 dated Mar. 22, 2016, 12 pages.
Supplementary European Search Report dated Jul. 26, 2018 in corresponding International Application No. 15876107.
Chinese First Office Action issued in Chinese Patent Application No. 201580071602.9 dated Jan. 28, 2019.
Chinese Second Office Action dated Aug. 8, 2019 corresponding to counterpart Patent Application CN 201580071602.9.
Australian Examination Report No. 1 dated Aug. 6, 2019 corresponding to counterpart Patent Application AU 2015374244.
Japanese Office Action dated Oct. 1, 2019 corresponding to counterpart Patent Application JP 2017-534653.

\* cited by examiner

SYSTEM AND METHOD FOR TREATING COPD AND EMPHYSEMA

BACKGROUND

1. Technical Field

The present disclosure relates to a system, and method of treatment of Chronic Obstructive Pulmonary Disorder (COPD) and particularly its two primary manifestations emphysema and chronic bronchitis. More particularly, the present disclosure relates to a system and method for enhanced navigation of an extended working channel or catheter and one or more energy application tools positionable there through in one or more branched luminal networks of the lungs to a target at the afflicted portions of the lungs to treat COPD.

2. Description of Related Art

Poor airflow that results from emphysema is often the result of a breakdown of lung tissues. In patients suffering from emphysema the alveoli are no longer elastic and can become enlarged due to walls between the alveoli breaking down. As a result, the alveoli lose their shape and become floppy. This damage from emphysema leads to fewer and larger air sacs instead of many tiny ones. These large alveoli may be called bullae. One result of this breakdown of the alveoli is that the volume of gas exchange that can occur is reduced as the surface area of these fewer enlarged alveoli is less than the many smaller alveoli. Additionally, the weakened floppy alveoli easily expand during an inhalation. Because of the weakened condition, that air having entered the weakened alveoli cannot be forced out of the lungs during exhalation. Deoxygenated air is trapped inside of the damaged floppy alveoli. This trapped air, however, keeps the alveoli expanded and thus takes up precious volume in the chest cavity. By taking up volume in the chest cavity, the volume available for inhalation of oxygenated air decreases effectively preventing the patient from ever satisfying their need for oxygen. A patient suffering from emphysema will typically appear thin, and take very rapid low volume breaths. As can be imagined the problem of easy filling and poor emptying of the lung leads to progressive hyperexpansion of the lungs, increased residual volume, reduced capacity, inefficient breathing mechanics, and in general a continually worsening patient condition as they struggle to inspire sufficient volume of air. The classic description is that the patient will appear as a "pink puffer," because the patient will be constantly working in an effort to inspire any oxygen into their overinflated lung tissues.

Chronic bronchitis is the result of excessive mucus build-up in the bronchioles. Often this mucus production is part of an inflammatory response caused by injury to the airways from smoking and other inhaled antagonists. The mucus can be so excessive that it overcomes the ability of the cilia within the lungs to sweep the mucus out and allow it to be expelled. Further, the mucus limits the size of the airways through which air must travel in the lungs, thus limiting the volume of air that can be inhaled. The combined effect causes a sufferer to persistently cough in a futile attempt to clear the mucus. This mucus can be so excessive that as it is drawn further and further distal in the lungs (e.g., to the alveoli which might not themselves be inflamed) the mucus limits the gas exchange as it coats the alveoli walls. The mucus reaching the alveoli further exacerbate the challenges of gas transfer experienced by smokers, where tar and other contaminates may already be covering the lining of the alveoli creating a barrier for gas exchange. Further, the mucus and other contaminants are a breeding ground for bacterial growth, further infection and even greater bronchitis symptoms. The classic description of someone suffering from chronic bronchitis is a "blue bloater." The color refers to the lack of oxygen successfully transferring from the alveoli to the blood stream and $CO_2$ being expelled from the blood stream through the alveoli to the atmosphere. These patients often appear bloated due obesity as well as water retention as a result of their compromised pulmonary and circulatory functions. As will be appreciated, many if not most patients will suffer from both emphysema issues and chronic bronchitis issues.

Fully functioning alveoli can often adapt and at least partially compensate for the reduction in total lung capacity caused by emphysema COPD. Indeed, this is one reason for the use of the highly invasive Lung Volume Reduction Surgery (LVRS) where wedges of damaged lung are removed to allow the remaining tissue to function better. In part this improved performance is enabled by the increase in space afforded the remaining alveoli to expand when the damaged portions of the lung are removed. By reducing the lung size, the remaining lung and surrounding muscles (intercostal and diaphragm) are able to work more efficiently. This makes breathing easier and helps patients achieve greater quality of life.

Aside from the highly invasive LVRS, the standard of care for lung diseases, such as asthma and COPD including emphysema and chronic bronchitis has been focused largely on pharmaceutical treatment modalities. For example, ADVAIR®, a bronchodilator is currently marketed by GlaxoSmithKline plc. for the treatment of COPD. Alternatively, it has been reported for decades that lung denervation via invasive means (e.g., surgery) may provide therapeutic benefit for asthma or emphysema. Again such surgical treatment is invasive and results in the disablement of whole or parts of functions of the nerve that affects contraction of the damaged alveoli.

While these treatment options are effective to a point, the primary prescription for patients suffering from COPD is simply the administration of oxygen. Oxygen can alleviate some symptoms but does nothing to treat the underlying diseases. Accordingly, additional treatment options are needed to increase the range of patients eligible to receive treatment and provide treatment options that yield a better result.

SUMMARY

The present disclosure is directed to a system and method enabling the receipt of image data of a patient, identification of one or more locations within the image data depicting symptoms of COPD, analyzing airways and vasculature proximate the identified locations; planning a pathway to the one or more locations, navigating an extended working channel to one of the locations, positioning a microwave ablation catheter proximate the location, and energizing the microwave ablation catheter to treat the locations depicting symptoms of COPD. In accordance with one aspect, the method includes placing the microwave ablation catheter proximate enlarged alveoli. Additionally or alternatively, the method can include placing the microwave ablation catheter proximate a region of the lungs where over production of mucus affects ventilation (V).

In accordance with a further aspect, the method includes temporarily and reversibly sealing at least one airway proximate at least one of the identified locations, and collapsing tissue in fluid communication with the sealed airway. This may be accomplished by applying a vacuum to the sealed airway such that air within the alveoli is removed. Alternatively, this may be accomplished by inserting needle ablation probes into the tissue and applying energy to create coagulated zones, and mechanically collapsing the tissue.

A further aspect of the disclosure is directed to coagulating the tissue of alveoli. This coagulation may be performed while the alveoli are in the collapsed state to thermally fix the alveoli and reduce its volume. The coagulation increases chest cavity volume into which untreated lung tissue can expand and increases the ventilation (V) of the untreated lung tissue.

Yet a further aspect of the disclosure is directed to sealing at least one pulmonary blood vessel associated with the alveoli. The pulmonary blood vessel may supply blood to an identified location depicting symptoms of COPD. By sealing the blood vessels a shunt is formed directing blood flow away from the sealed pulmonary blood vessel to untreated portions of the lungs. This shunting has the effect of increasing the perfusion (Q) of the blood supply to untreated lung tissue.

These and other aspects of the disclosure are described in detail in the following detailed description and drawings.

DETAILED DESCRIPTION

The present disclosure is directed, in part, to the treatment of COPD both emphysema and chronic bronchitis through the use of microwave ablation techniques. Placement of the microwave ablation probes is enabled through the use of an Electromagnetic Navigation (EMN) System. By ablating tissue of the lungs afflicted by emphysema or chronic bronchitis the tissue that had previously been ineffectively exchanging gas due to its loss of elasticity, destroyed alveoli walls, mucus and other contaminants creating a barrier, and other issues, is necrosed causing the tissue to retract and shrink. The shrinkage forces the air which was previously trapped in the damaged alveoli to be expelled and prevents new air from entering that space. Additionally the overall shrinkage allows portions of the lungs which are operating more effectively to expand into the newly available area and provide for greater amounts of gas exchange. This increases the ventilation (V) (volume of air reaching the alveoli) enabling more oxygen to reach the blood supply. A similar mechanism for action is employed in LVRS.

Another effect of ablation process is the sealing of blood vessels. The lungs include two blood supplies, one pulmonary for gas exchange and one systemic for supplying the tissues of the lungs, selective sealing of pulmonary blood vessels can effectively shunt the blood supply away from the treated areas and to portions of the lung which are better functioning. This shunting provides an effective increase in perfusion (Q) (the amount of blood reaching the functional alveoli). While total volume of blood flow might not actually increase for a given heart rate, because the entirety of the volume is reaching better performing tissues, the effect is the same as if the blood supply to the remaining portions of the lung had been increased, specifically gas exchange is increased. Both of these mechanisms for action, as well as systems, devices, and methods of achieving them as well as other aspects of the present disclosure are described in detail below.

Figure 1A:
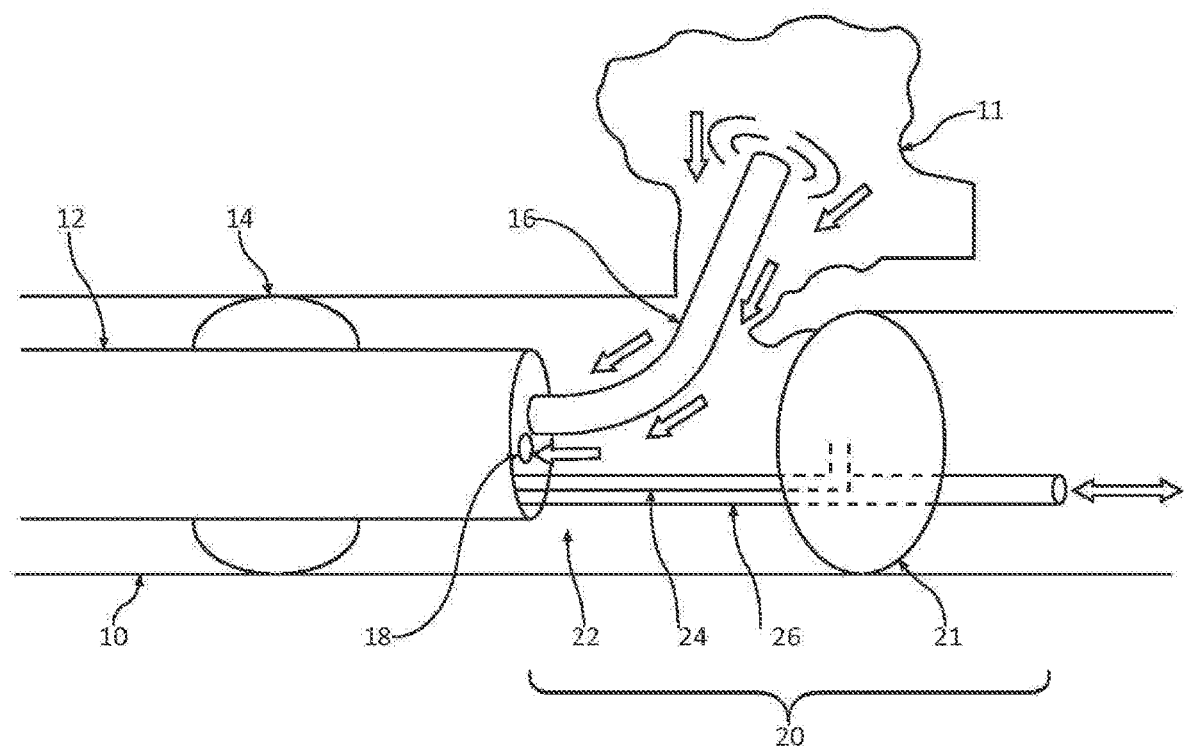
FIG. 1A is an internal view of a an airway receiving treatment in accordance with the present disclosure.

FIG. 1A depicts one embodiment of the present disclosure. Specifically, FIG. 1 depicts an airway 10, having an alveolus 11 branching therefrom. Inserted into the airway 10 is an extended working channel (EWC) 12 of the type commonly used to navigate distal regions of the lungs where a bronchoscope cannot navigate. A system employing such EWC is described in greater detail below. Extending laterally from the EWC 12 is a proximal balloon 14. The proximal balloon 14 seals the airway 10 proximal of the distal end of the EWC 12. Extending from the distal end of the EWC 12 is a microwave ablation catheter 16. The microwave ablation catheter 16 may house a microwave ablation antenna (See FIGS. 11 and 12), for example, a water-jacketed microwave ablation antenna, for the treatment of tissue. Located on the EWC 12 is a vacuum port 18. The vacuum port 18 is in fluid communication through the EWC 12 to a vacuum source (not shown). Extending from the EWC 12 is a balloon catheter 20, including a distal balloon 21, and a dual fluid line 22 having first and second fluid lines 24 and 26. The distal balloon 21 is expanded by the application of fluid via the first fluid line 24. The second fluid line is passes through the distal balloon 21 and fluidly connects portions of the airway 10 with atmosphere or a ventilation device (not shown) permitting portions of the lung distal (e.g., closer to the pleura boundaries) to receive and expel air. The proximal and distal balloons 14 and 21 create an area in airway 10 which is effectively sealed from the atmosphere.

In instances where alveolus 11 is determined to be enlarged as a result of emphysema or is determined to be suffering the effects of chronic bronchitis or other conditions limiting gas transfer, the microwave ablation catheter 16 may be inserted into or proximate the alveolus 11. Once so placed, a vacuum may be draw via the vacuum port 18. As a result of this vacuum, the air within the alveolus 11 will be withdrawn and the alveolus effectively collapsed. This collapse is also referred to as induced atelectasis. The collapse of the alveolus 11 or tissue affected by the applied vacuum causes the tissue to collapse around the microwave ablation catheter 16. It should be noted that while a single alveolus is referred to with reference to FIG. 1, one skilled in the art will recognize that do to normal collateral ventilation, multiple alveoli will likely be affected by these methods and the use of singular or plural should not limit the scope of this disclosure. This collapse (i.e. removal of air) largely homogenizes the dielectric constant of the area to be treated by the microwave ablation catheter 16, resulting in consistent treatment effects and more predictable outcomes. Alternatively or additionally, a liquid, such as sterile saline could also be injected into the Alveolus to again homogenize the dielectric constant of the area and increase the susceptibility of the area to be treated (e.g., the lung parenchyma). Susceptibility refers to the ability of a material to convert the microwave energy into heat. In this case the heat is used for sealing of the alveolus and or blood vessels (including microvasculature) in the alveolus. By placing the tissue first under a vacuum and subsequently injecting the sterile saline, the tissue may be more receptive to absorption of the sterile saline resulting in greater susceptibility of the tissue. Application of microwave energy ablates the alveolus 11 or tissue proximate the alveolus. This ablation or coagulation may be performed while the alveolus is in the collapsed state to thermally fix the alveolus in the collapsed state and reduce its volume. Ablation of the tissue causes the proteins to denature and a general breakdown of the cell membranes resulting in the formation of a mass of coagulum which may be absorbed by the body over time, an importantly is no longer able to carry on any physiological function. This process may be referred to as coagulation-necrosis.

Generally coagulation is thought to begin when the tissue temperature reaches about 45° C., the duration of energy application substantially decreases as the temperature increases to between 50 and 55° C., and necrosis occurs nearly immediately at temperatures between 60-100° C., above 100° C. tissue actually vaporizes and carbonizes. Control of the power and duration of application of energy from a microwave generator (described below), enables the effective control of heat absorption profiles and selective treatment of tissue.

Coagulation-necrosis when specifically targeted within the lungs has two beneficial effects. In the case of a patient suffering from emphysema, the afflicted alveolus 11 or even larger parts of the lungs can be effectively fused resulting in a decreased volume of dead air space within the chest cavity. Secondly, the coagulation-necrosis can effectively seal blood vessels, particularly pulmonary blood vessels which are directing blood flow to portions of the lungs which have become ineffective whether as a result of emphysema or chronic bronchitis or other conditions. If properly targeted, the systemic blood vessels may be retained such that while removed from the pulmonary functions of respiration, lung tissues do not degrade from a lack of systemic blood flow, particularly those distal the treated area. Additionally pulmonary blood flow to areas distal the treated area is preserved. Further, in some instances, it may be desirable to seal or otherwise degrade the systemic blood vessels (for example those solely within an alveolus that is treated) in order to promote the tissue destruction of the alveolus or other treated areas.

In accordance with the present disclosure, by targeting the microvasculature of an area to be treated (e.g., blood vessels of less than 1 mm) the blood flow to certain areas of the lungs may be effectively skeletonized as will be described in some detail with respect to FIG. 2. By skeletonization, the present disclosure seeks in part to describe systems and methods where smaller blood vessels are sealed, but the larger blood vessels are not. This enables these larger blood vessels to continue supplying blood more distally into the lungs, while the smaller blood vessels, those more likely to be directly supplying blood to affected areas, and which are ineffective at gas exchange, to be sealed. As outlined in greater detail below, this skelotinization is achieved by close control of placement of treatment devices, power and duration of treatment, and other factors which help control and closely target the desired treatment areas. Part of the planning process described herein is determining whether to completely coagulate and seal an alveolus, as described above, whether to treat an area such that all the vasculature in that area below a certain size is sealed, effectively skeletonizing it, or whether another treatment option or combination is best for a given circumstance.

As a result, the above identified procedure treats not only the ventilation (V) but also the perfusion (Q). Ventilation is increased by reducing the volume of the lungs which is ineffective for respiration (e.g., enlarged alveoli) allowing other portions of the lung to expand to fill the increased volume. Secondly perfusion is increased as a result of the shunting effects of coagulating blood vessels utilized for pulmonary functions. The blood flow which would otherwise be directed to these ineffective portions of the lungs is now being shunted to areas which have greater effectiveness. Much like the volumetric increases which aid the increases in V, the lungs have the ability to greatly expand their volumetric blood flow Q without substantial increases in blood pressure. In some instances this may be a four-fold volumetric increase without a substantial increase in pressure within the lugs (e.g., when running very hard). As a result, the shunting of blood from ineffective portions of the lung to effective portions of the lungs results in greater gas transfer at a constant volumetric flow, without an increase in blood pressure.

Exemplary microwave ablation antenna architecture that might be used within microwave ablation catheter 16 is described for example in co-pending U.S. Published Application No. 2014/0046315 entitled "Microwave Ablation Catheter and Method of Utilizing the Same," filed Mar. 15, 2013; U.S. Published Patent Application No. 2014/0276739 entitled "Microwave Energy-Delivery Device and System," filed Mar. 15, 2013; U.S. Published Patent Application No. 2014/0290830 entitled "Step-Down Coaxial Microwave Ablation Applicators and Methods for Manufacturing Same," filed Mar. 28, 2014; and U.S. application Ser. No. 14/831,467 entitled "Systems and Method for Spherical Ablations," filed Aug. 20, 2015 the entire contents of each are incorporated herein by reference. Further details of an exemplary microwave ablation antenna are detailed below.

Figure 1B:
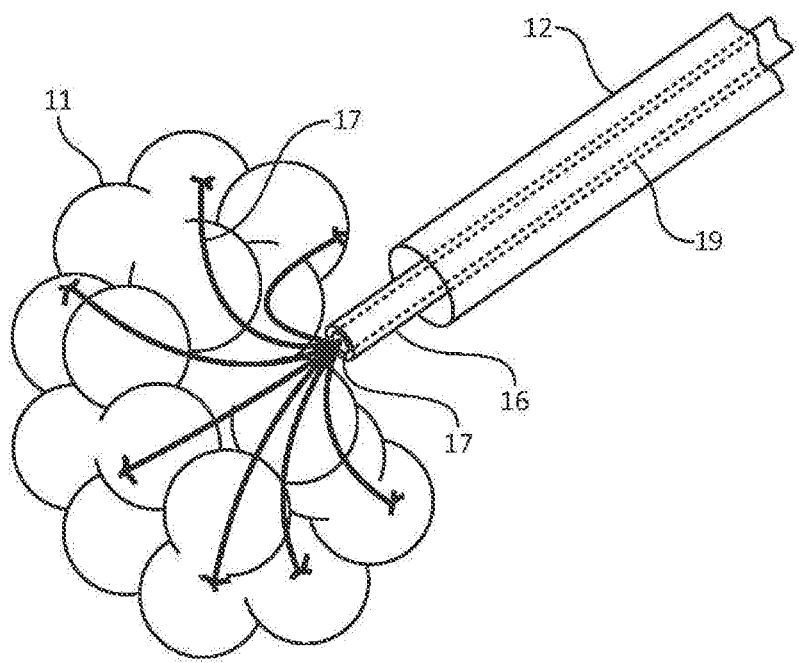
FIGS. 1B and 1C are view of a an airway receiving treatment in accordance with the present disclosure.
Figure 1C:
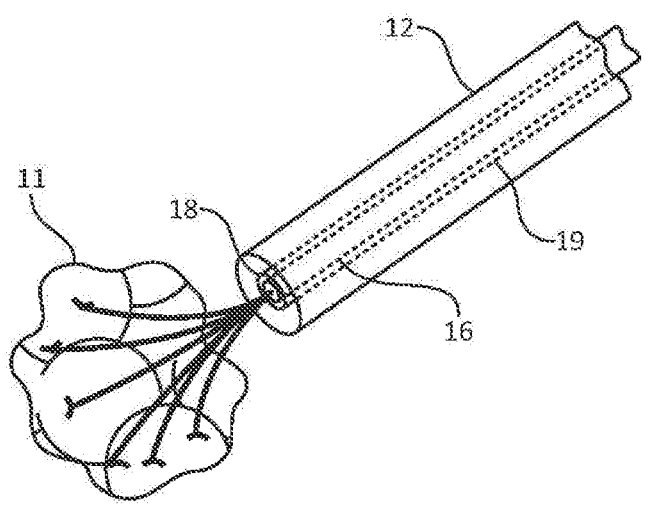

FIG. 1B depicts a modification of the embodiment in FIG. 1A, rather than relying on vacuum alone to reduce the size of the alveolus 11, a more mechanical approach can be undertaken. As with FIG. 1B the EWC 12 is navigated proximate the alveolus 11 in question, but rather than extending a single microwave ablation catheter 16 with a single energy radiator, a plurality of small needle like ablation probes 17 can be housed in the ablation catheter 16 and released into the alveolus 11, as shown in FIG. 1B. The ablation probes 17 may be needle like or may have small hooks or barbs to engage the tissue. The alveolus 11, as noted above, is not particularly resilient and they are structurally weak. By energizing the ablation probes 17, small areas of coagulation can be formed in the walls of the alveoli. The areas of coagulation have greater structural properties than untreated areas. The barbs or hooks, or localized charring and sticking of tissue to the ablation probes 17 allow for mechanical force to be applied to this newly resilient coagulum in the treated tissue. By retracting the ablation probes 17 back into the ablation catheter 16, the size of the alveoli can be greatly reduced in advance of further treatment as shown in FIG. 1C. This may be performed mechanically or in combination with the application of vacuum from vacuum portion 18. Once drawn together, the ablation probe shown in FIG. 1B may be extracted. The alveolus 11 should remain in a contracted state by application of the suction through vacuum port 18. A second microwave ablation catheter 16 may then be inserted to enable further treatment as described in conjunction with FIG. 1A above. Those of skill in the art will recognize that in this embodiment the ablation probes 17 may be microwave ablation probes or radio frequency (RF) ablation probes without departing from the scope of the present disclosure. RF ablation probes enable current-based thermal ablation and require connection to an RF generator (not shown).

As with the embodiment of FIG. 1A, in the embodiment of FIG. 1B, sterile saline or another fluid may be injected into the treatment area in order to increase the susceptibility of the in the area to be treated. If using RF ablation, the injection of saline will also reduce the impedance barrier of the tissue resulting in improved thermal ablation efficiency. An iterative technique may be employed whereby following suction of the air, sterile saline is injected into the alveolus causing it to re-expand. At this point the ablation probes 17 may be inserted into the tissue of the alveolus and energized. The saline reduces the impedance and promotes efficient thermal ablation. After energization, the ablation probes 17 can be retracted and the cycle repeated with suction, saline injection, insertion of the ablation probes 17 and energization. By performing this multiple times the structure of the alveolus can be altered to increase its toughness and reduce the floppiness of the over inflated alveolus. Further, the repeated targeted ablations can achieve the same vessel sealing and volume reductions as described elsewhere herein. Though described here with respect to RF, microwave ablation probes could also be used Similarly, in more of a laparoscopic surgical approach, spot ablations can be formed on the outside surfaces of portions of the lungs and used to create points for mechanical deformation of the lung. Such an approach may be particularly useful where very large sections of the lungs are in need of mechanical deformation. Further a combined internal and external approach could be used in a triangulated fashion in order to produce a desired result.

Figure 2:
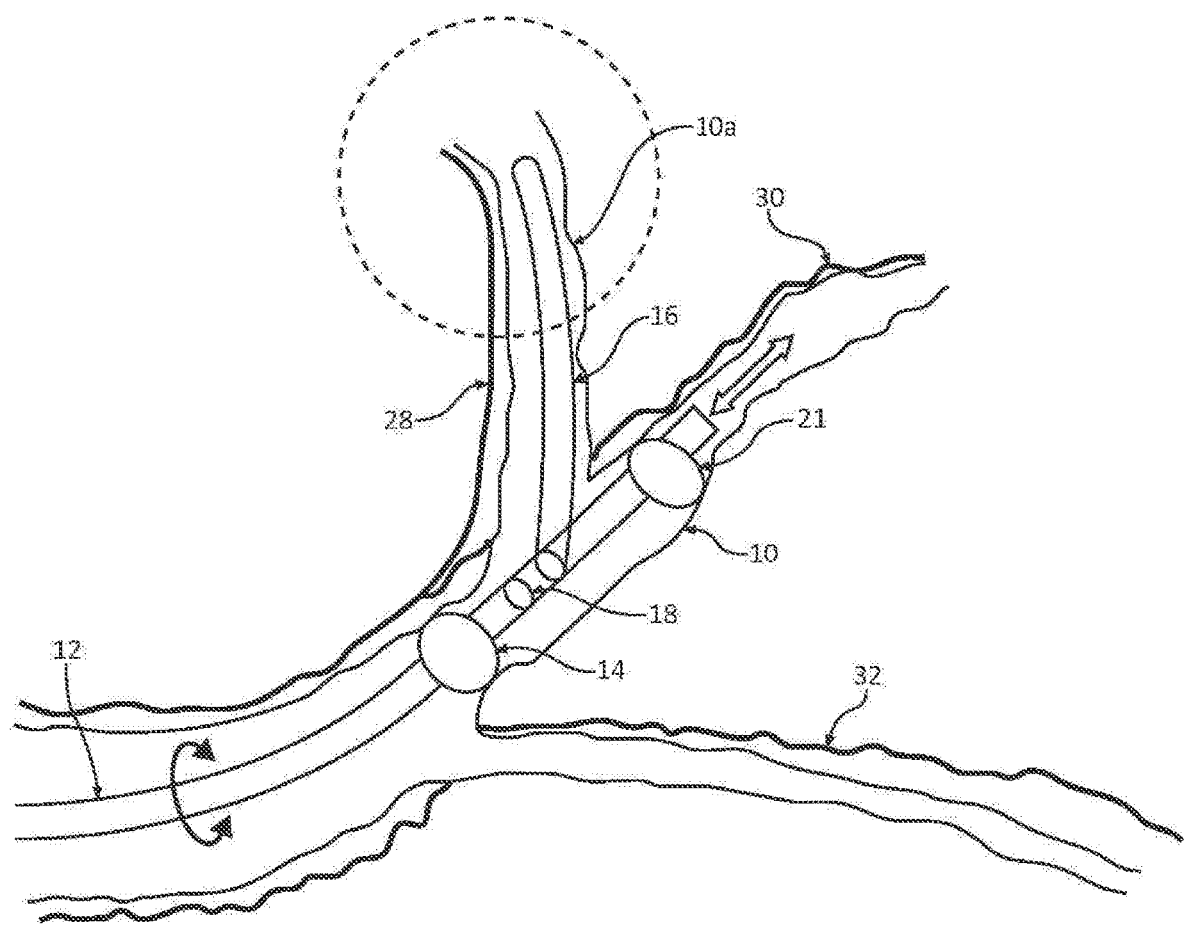
FIG. 2 is an internal view of a an airway receiving treatment in accordance with the present disclosure.

FIG. 2 depicts a different arrangement of the EWC 12, where rather than exiting a distal end of the EWC 12, the microwave ablation catheter 16 exits between the proximal balloon 14 and the distal balloon 21. The EWC retains sufficient space therein to permit airflow to areas further distal in the lungs. Proximal and distal balloons 14 and 21 expand to effectively seal airway 10a from other portions of airway 10. The microwave ablation catheter 16 extends into an airway some distance from the EWC 12. Suction, possibly in combination with sterile saline, may be selectively applied via vacuum port 18. However, as shown the example in FIG. 2 is primarily related to selective treatment of blood vessel 28 without affecting related downstream blood vessel branch 30. By moving the treatment zone 32 to a location sufficiently removed from blood vessel 30, and identifying an appropriate power and duration for treatment the blood vessel 28 can be effectively sealed without damaging blood vessel 30. The result is that the blood which would have originally flown through blood vessel 28 will now flow through blood vessel 30 and blood vessel 32 (and other vessels) resulting in an effective increase in Q which will promote gas exchange by sending blood only to those areas identified as capable of functioning effectively.

FIG. 2 depicts a usage of the microwave ablation catheter 16 where projection and control of the microwave energy can result in heating and sealing of blood vessel 28, without irreversible damage to the walls of airway 10a. This may be accompanied with the use of one or more cooling agents being applied to airway 10a. These cooling agents may be flood airway 10a using the vacuum port 18 as a path for entry and subsequent removal after treatment. Techniques for such focal ablations are described for example in U.S. Pat. No. 8,636,664 to Brannan entitled "Energy-delivery device including ultrasound transducer array and phased antenna array, and methods of adjusting an ablation field radiating into tissue using same," the entire contents of which is incorporated herein by reference. Such techniques for focal ablation can be performed either with or without localized ultrasound imaging systems to ensure proper placement and observe the effects of the treatment.

With the above described effects of heating to between 45 and 60° C. to achieve coagulation, effective coagulation and occlusion of blood vessels up to 3 mm in diameter can likely be achieved in about 5 minutes at 100 W of power. As a result, multiple sites can be relatively rapidly treated within the patient, and the patient should experience nearly immediate changes in V and Q thus improving lung function and reducing the symptoms of emphysema and chronic bronchitis.

Figure 3:
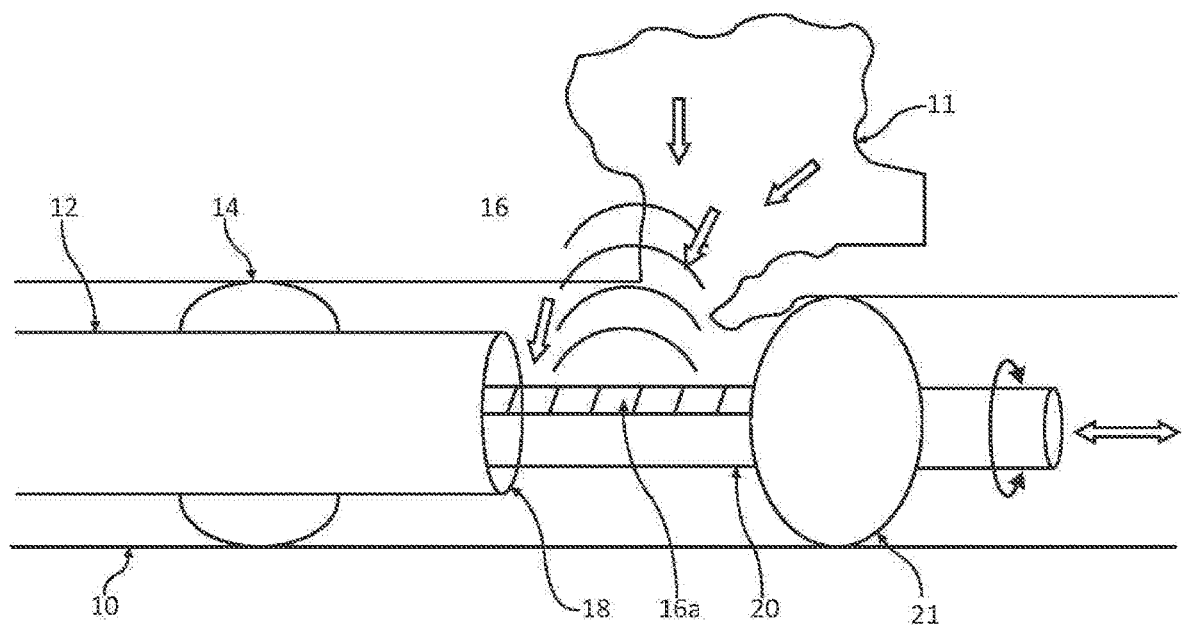
FIG. 3 is an internal view of a an airway receiving treatment in accordance with the present disclosure.

FIG. 3 depicts a further embodiment of the present disclosure in which a directional microwave ablation catheter 16a exits from EWC 12. The distal end of the EWC 12 acts as the vacuum port 18. In such a system the EWC 12 would be navigated proximate the desired location here near alveolus 11. Once approximately located and proximal balloon 14 is expanded, the microwave ablation catheter 16a, which may be formed as part of a balloon catheter 20 can be extended from the EWC 12. The balloon catheter 20 may be rotated to appropriate place the directional microwave ablation antenna 16a such that it is directed at the tissue for treatment. Once rotation is complete, the distal balloon 21 may be inflated to secure the directional microwave ablation catheter 16a in the proper location and treatment may be undertaken. Again the suction may be applied from a vacuum source (not shown) through vacuum port 18 in the distal end of the EWC to achieve collapse of alveoli and homogenization of the dielectric constants by pulling the tissue to be treated proximate the microwave ablation catheter 16a. Under certain conditions, the homogenization leads to increase in dielectric constants for the treatment area which in turn leads to shorter microwave wavelengths and improved focal delivery of energy. Further, the collapse, either alone or in combination with the injection of fluid such as sterile saline increases the susceptibility of the area to be treated promoting greater efficiency in the conversion of the microwave energy to heat. Throughout the setup and treatment distal regions beyond the distal balloon 21 may still receive airflow through the open distal end of the balloon catheter 20.

Referring back to FIG. 2, though the microwave ablation catheter 16 is described as exiting from the EWC 12, the present disclosure is not so limited. The microwave ablation catheter 16 may exit from an intermediate catheter such as the balloon catheter 20 as depicted in FIG. 3, with the vacuum port being positioned as shown in FIG. 3. Such an arrangement may make placement and rotation of the microwave ablation catheter properly within the airway for treatment as shown in FIG. 2. These and other refinements to the mechanical aspects of the present disclosure as would be apparent to one of ordinary skill in the art are considered within the scope of the present disclosure.

As a result of the collapse of the alveolus 11 or other tissue, the removal of air to homogenize the dielectric constant in the treatment area, and the use of one or more of the microwave ablation antenna architectures described herein highly controllable spherical ablations can be formed. The repeatability of these ablations lend themselves to pre-procedure planning to enable the accurate placement of the microwave ablation catheters 16 to achieve the desired treatments described herein.

Figure 4:
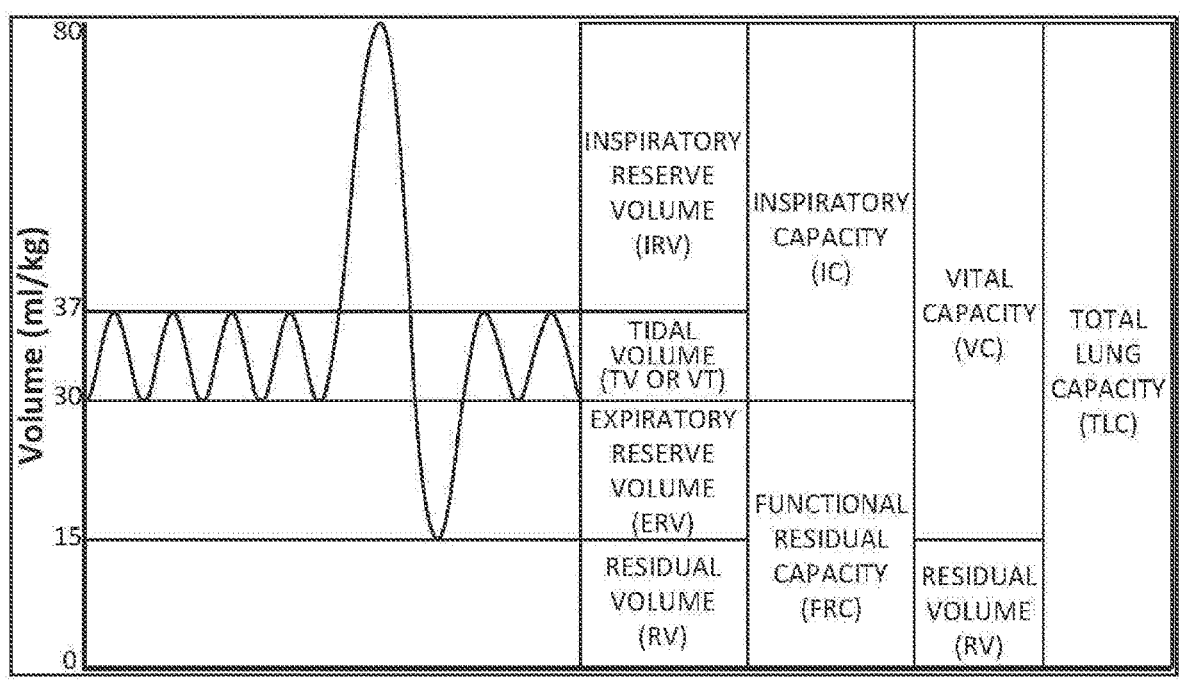
FIG. 4 is a chart of lung volumes and capacitates.

A further aspect of the present disclosure is directed to a system and method for identifying locations for treatment and measuring the effect of the treatment. A first step in such a system is the performance of a pulmonary function test (PFT). The PFT may include physical examination, chest x-rays and tests of pulmonary function. These tests of pulmonary function including spirometry which tests the lungs mechanics and abilities. Further tests can be used to determine the four lung volumes and the four lung capacities. A graph of these eight volumes and factors along with a respiration chart is shown in FIG. 4. Maximum inspiratory and expiratory pressures can be measured, oxygen desaturation can be measured using the six-minute walk test, and an analysis of the arterial blood gases can be undertaken. With this information, an understanding of the effects of the condition and the challenges the patient is facing can be determined.

Following the PFT a computed tomography (CT) scan of the lungs can be undertaken. This CT scan which could be a cone beam CT scan can serve several purposes. As an initial matter, the results of the images generated from the CT scan can be analyzed to identify areas of hypodensity. That is areas where the density of the tissue is less than the surrounding tissue. This may be particularly useful for patients suffering from emphysema as the expanded floppy alveoli or bullae will provide images that have areas which may be substantially black, indicating that they are largely air with little to no tissue separating these enlarged alveoli. Because of this hypodensity, image analysis using 3D image processing is particularly useful as identification of the areas where the densities of the images (measured in Hounsfield units or HU) is below a certain threshold (e.g. −950 HU) approximately the same as air. This 3D rendering is relatively straightforward and even coarse thresholding can be employed to distinguish the enlarged alveoli from tissue and identify their locations in the CT images. These coarse thresholded values can then be rendered as a 3D model of the affected areas of the lungs.

Figure 5:
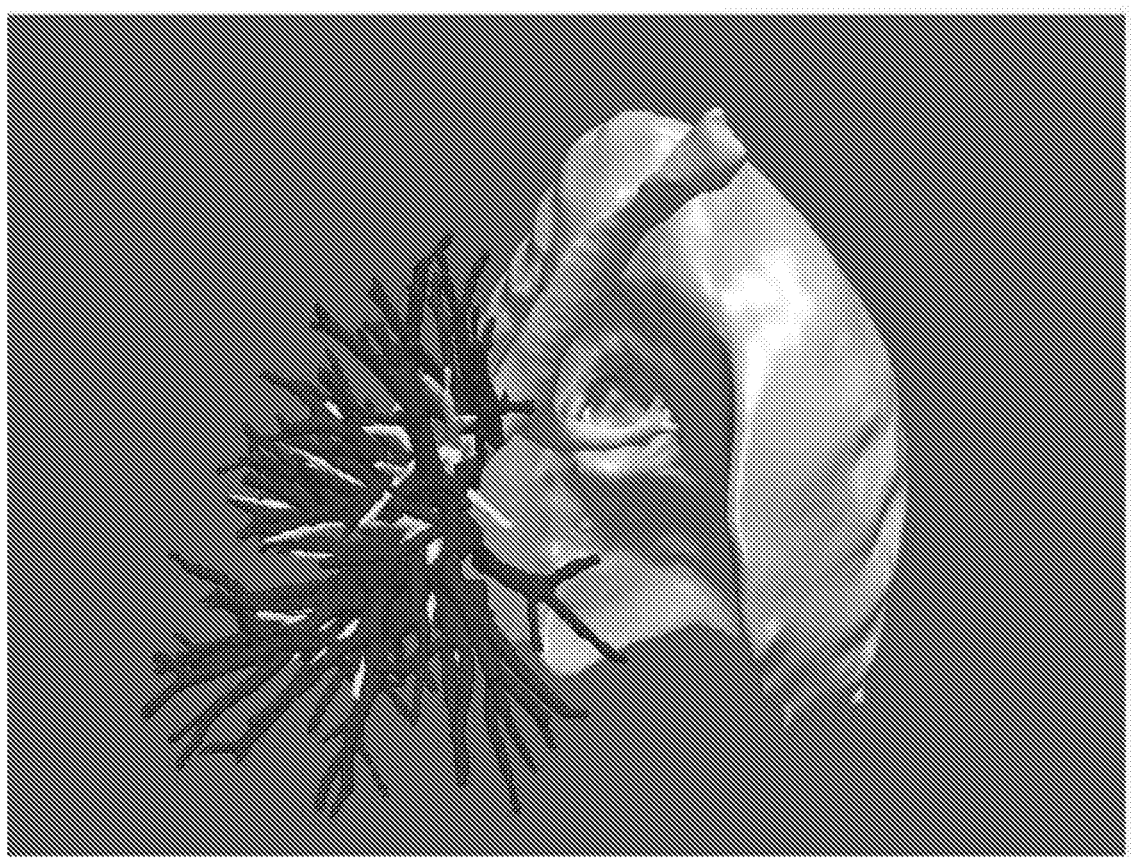
FIG. 5 is a 3D rendering in accordance with the present disclosure depicting airways, and blood vessels in the lungs for use with planning an navigation software applications.

Separately, the CT image data may be processed to identify all of the vascular structure within the lungs. Again a 3D model of this vasculature can be generated. An example of the 3D mapping of vasculature from CT images is shown in FIG. 5, which depicts the vasculature of a right lung and a volume and surface rendering of the left lung. Techniques for generating 3D volumetric renderings are described in U.S. patent Ser. No. 14/821,950, entitled "Treatment Procedure Planning System and Method, filed Aug. 10, 2015, the entire contents of which are incorporated herein by reference. As will be appreciated, the generation of a 3D map of the vasculature may be more challenging than of the hypodense areas. As an alternative to generation of a 3D map of the vasculature from the CT scan, an angiogram or a CT angiogram may be separately undertaken. In an angiogram radiographic fluids are injected into the patient, and used to identify the precise location of the vasculature in the images. The identification of the vasculature is made much easier by the addition of these radiographic fluids as they resolve themselves much more clearly in the X-ray and CT images. Where a CT angiogram is undertaken, the images of the vasculature can be registered to the images mapping the hypodensities in the lungs to create a composite image set revealing the interaction of the vasculature with the hypodense areas.

A further alternative embodiment of the present disclosure utilizes metabolic imaging techniques such as Positron Emissions Tomography (PET). PET using an ingested or injected radioactive material images metabolic activity. Areas of high metabolic activity have high emissions and areas with low metabolic activity have low emissions. Many devices perform a combined PET/CT imaging technique which has proven to be quite accurate. As relates to the present disclosure, the PET/CT scan can initially be used to identify areas in the lungs which show very little metabolic activity. These areas should closely correspond to areas of over inflated alveoli. There is very little metabolic activity in these areas because they are mostly comprised of air. In this way, a PET/CT image set can be utilized to identify the hypodense areas to which navigation and treatment should be directed.

By careful analysis of the vasculature and its interaction with the hypodense areas, determinations can be made as to the identity of vasculature that might be affected by treatment using microwave ablation. This analysis can identify locations where a blood vessel is to be sealed creating a shunt preventing the blood from continuing circulate through the blood vessel. The analysis can identify blood vessels that despite being in proximity to the area to be treated are too large and will experience too large a heat sink effect due to blood flow to be affected by the ablation. As a result, despite being proximate the ablation zone these blood vessels are not in danger of being sealed or coagulated and effectively starving all distal regions of blood through that blood vessel. Again, as an example, only blood vessels smaller than 3 mm might be targeted and the treatment limited to about 100 W at 5 minutes to control the size of the ablation zone.

Still further, as noted above, because the microwave ablation catheters 16 contemplated by the present disclosure can be accurately controlled, and in many instances generate spherical ablation zones, a complete ablation plan of intersecting ablations can be generated to ensure that all of the tissue desired to be treated can be treated while minimizing the treatment effects on healthy tissue.

Figure 6:
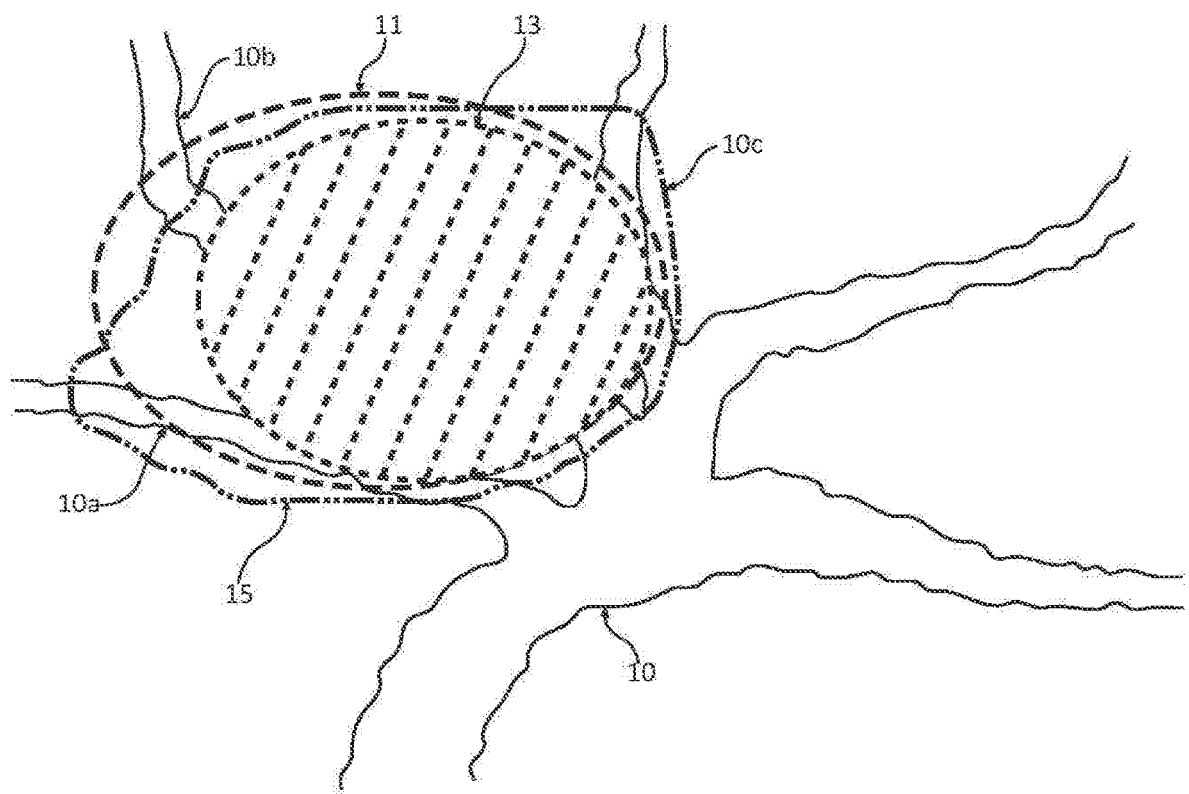
FIG. 6 is an internal view of a an airway receiving treatment in accordance with the present disclosure.

FIG. 6 depicts an area of the vasculature of the lungs being treated in accordance the methods depicted in conjunction with FIGS. 1-3. In FIG. 6, a hypodense area 11 is depicted spanning a variety of blood vessels 10a, 10b, 10c. Blood vessels 10a and 10c are less than 3 mm in diameter. Blood vessels 10 and 10b are larger than 3 mm. As a result when a microwave ablation catheter 16, as depicted in FIGS. 1-3, into airways proximate the blood vessels such that upon activation an ablation zone 13 is generated, the result coagulation zone encompasses blood vessels 10a and 10c but does not seal blood vessel 10 or 10b. However, by coagulating the blood vessels 10a and 10c an enlarged treatment zone 15 is created. This treatment zone encompasses an area which is in this instance not exactly coextensive with the hypodense area 11, but which treats the vasculature which feeds the hypodense area. In addition, because of the size of the blood vessels 10 and 10b, effect on healthy tissue outside of the hypodense area is minimized and blood continues to flow through these blood vessels including 10b despite running directly through the ablation zone. Those of skill in the art will recognize that while being depicted as a 2D representation, such treatment zones and the hypodense area are in fact 3D spaces and can be depicted as 3D volumes similar to those shown in FIG. 5 without departing from the scope of the present disclosure. Further, though depicted in simplified form, one of skill in the art such as a clinician will be able to identify those vessels likely to be related to the pulmonary aspects of the lungs and those related to systemic supply of blood to the lungs for the maintenance of the tissues such that the treatment described with respect to FIG. 6 is focused on treating the pulmonary blood vessels.

As will be appreciated by those of skill in the art, volumetric reductions and vascular sealing or occlusions have been separately described herein, however, they are both natural results of microwave ablation, thus for example, though FIG. 1 is described only with reference to volume reduction, blood vessels proximate the tissue being treated, particularly the microvasculature which is where gas exchange occurs will be treated and sealed as well. The result is that while treating for volume reduction treatment of blood flow shunting will also occur, similarly when treating for blood flow shunting some amount of volume reduction may also be experienced. For early stage patients this volume reduction may not be as important as for later stage patients, but will result regardless at least to some degree.

A further aspect of the present disclosure is a software application wherein the ablation zone 13 is depicted on images (2D or 3D) or models and the clinician is able to adjust and modify the expected ablation zone to best limit damage to healthy tissue, and maximally treat diseased tissue. The ablation zone 13 may change as more power or duration is selected, and the software application can analyze the vasculature and identify likely treatment zones 15. This will enable the clinician to optimize the ablation zone 13 and minimize the undesirable effects on healthy tissue, particularly that tissue that is further distal along the vasculature than the ablation zone 13. Further, the software application described above may include a user input, a sliding scale for example, which allows the clinician to modify the treatment zone based on a preference for volume reduction or vascular occlusion in a particular ablation zone. In certain instances the clinician may be presented with presentations where a choice must be made to perform one or the other in order to best preserve healthy tissue, and the software application can provide guidance into its determination of the best course of action based on a predetermined minimum ratio of diseased vs. healthy tissue impacted by the treatment. Additional metrics may include a ratio of diseased volume treated to total volume of tissue treated. For example a minimum cut-off may be set at 50% thus limiting proposed ablation plans to only those where more than half of the tissue treated is diseased.

Figure 7:
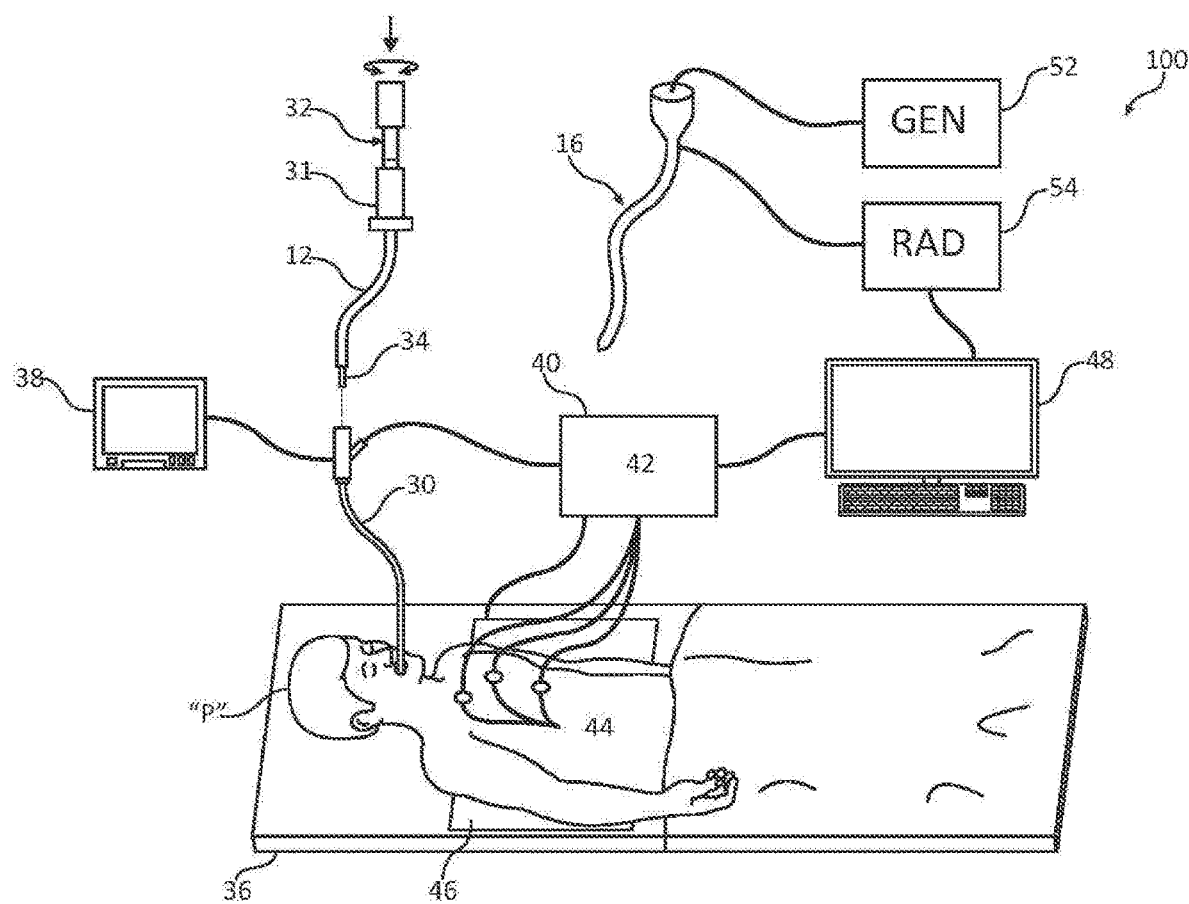
FIG. 7 is a perspective view of one illustrative embodiment of an electromagnetic navigation (EMN) system in accordance with the present disclosure.

FIG. 7 depicts an Electromagnetic Navigation (EMN) system 100 configured for reviewing CT image data (such as that described above with respect to hypodensity and vascular tree identification) to identify one or more targets, planning a pathway to an identified target (planning phase), navigating an extended working channel (EWC) 12 to the target (navigation phase), and confirming placement of the EWC 12 within the target. One such EMN system is the ELECTROMAGNETIC NAVIGATION BRONCHOSCOPY® system currently sold by Medtronic.

As shown in FIG. 7, extended working channel 12 is part of a catheter guide assembly 31. In practice, the extended working channel 12 is inserted into bronchoscope 30 for access to a luminal network of the patient "P." Specifically, EWC 12 of catheter guide assembly 31 may be inserted into a working channel of bronchoscope 30 for navigation through a patient's luminal network. A locatable guide (LG) 32, including a sensor 34 is inserted into the extended working channel 12 and locked into position such that the sensor 34 extends a desired distance beyond the distal tip of the extended working channel 12. The position and orientation (6 DOF) of the sensor 34 relative to the reference coordinate system, and thus the distal end of the extended working channel 12, within an electromagnetic field can be derived. Catheter guide assemblies 31 are currently marketed and sold by Medtronic under the name SUPERDIMENSION® Procedure Kits, or EDGE™ Procedure Kits, and are contemplated as useable with the present disclosure. For a more detailed description of the catheter guide assemblies 40, reference is made to commonly-owned U.S. Published Patent Application No. 2014/0046315 filed on Mar. 15, 2013 by Ladtkow et al, and U.S. Pat. No. 7,233,820, the entire contents of both are hereby incorporated by reference.

Figure 8:
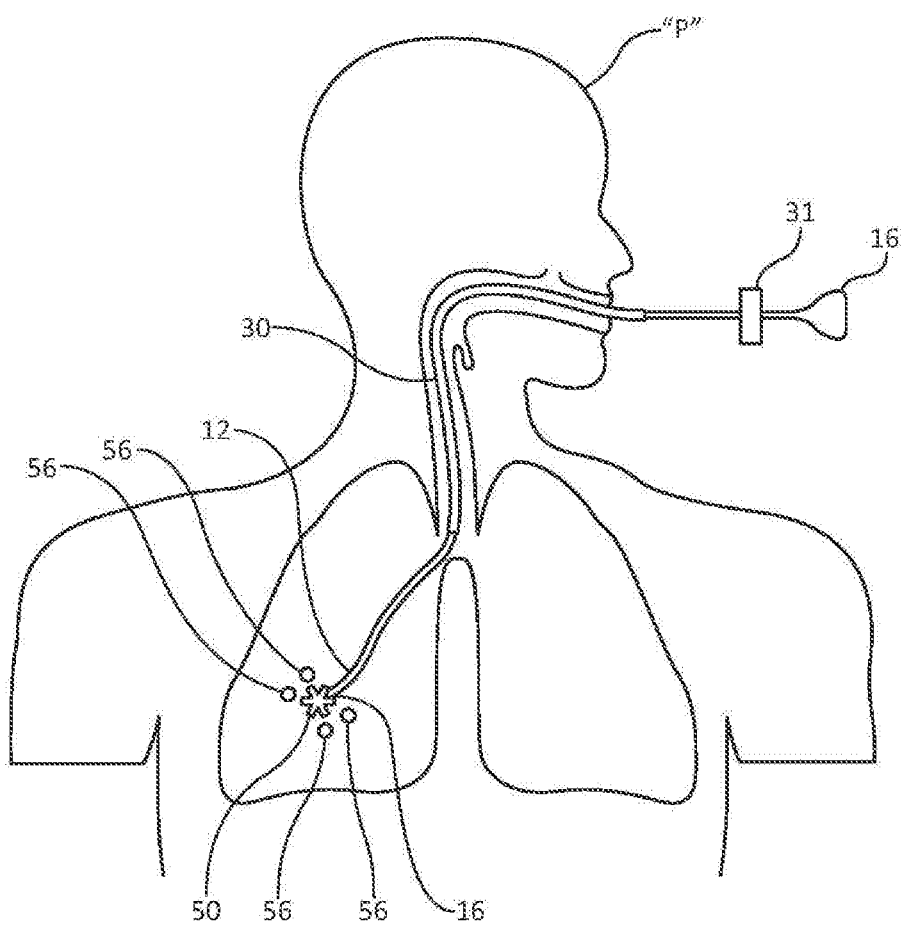
FIG. 8 is a perspective view of one illustrative embodiment of an extended working channel and microwave ablation probe treating a damaged portion of the lungs.

System 100 generally includes an operating table 36 configured to support a patient "P;" a bronchoscope 30 configured for insertion through the patient's "P's" mouth into the patient's "P's" airways; monitoring equipment 38 coupled to bronchoscope 30 (e.g., a video display, for displaying the video images received from the video imaging system of bronchoscope 30); a tracking system 40 including a tracking module 42 a plurality of reference sensors 44, and a transmitter mat 46 (also called an EM filed generator); and a computing device 48 including software and/or hardware used to facilitate pathway planning, identification of target tissue, navigation to target tissue, confirmation of placement of an extended working channel 12, or a suitable device there through (e.g., microwave ablation catheter 16), relative to a target 50 (FIGS. 6 and 8) and monitoring the application of microwave energy into a target 50.

Continuing with reference to FIG. 7, system 100 further includes a microwave ablation catheter 16 insertable into the extended working channel 12 to access a target 50. The microwave ablation catheter 16 is coupled to a microwave generator 52. In one embodiment, the microwave ablation catheter 16 is also coupled to radiometer 54 which is useable to detect changes in the condition of the tissue as described in greater detail in commonly owned and co-pending U.S. patent application Ser. No. 14/831,983 entitled "System and Method for Planning, Monitoring, and Confirming Treatment," filed Aug. 21, 2015, the entire contents of which are incorporated herein by reference. Although radiometer 54 is illustrated as being a separate component from microwave ablation device 16, in embodiments, radiometer 54 may be incorporated into microwave ablation catheter 16 or the microwave generator 52. Microwave generator 52 is configured to supply microwave energy to the microwave ablation catheter 16 to ablate a target 50. An exemplary microwave generator 52 is the EMPRINT™ Microwave Ablation System currently sold by Medtronic. Further details regarding the microwave ablation catheter 16 will be described in greater detail below with reference to FIGS. 8 and 9.

Computing device 48 may be any suitable computing device including a processor and storage medium, wherein the processor is capable of executing instructions stored on the storage medium. The computing device 48 may further include a database configured to store patient data, CT data sets including CT images, navigation plans, and any other such data. Although not explicitly illustrated, the computing device 48 may include inputs, or may otherwise be configured to receive, CT data sets and other data described herein. Additionally, computing device 48 includes a display configured to display graphical user interfaces such as those described below. Computing device 48 may be connected to one or more networks through which one or more databases may be accessed.

With respect to a pathway planning phase, computing device 48 utilizes computed tomographic (CT) image data for generating and viewing a three-dimensional model of the patient's "P's" airways, enables the identification of a target 50 on the three-dimensional model (automatically, semi-automatically, or manually), and allows for determining a pathway through the patient's "P's" airways to the target 50. More specifically, the CT scans are processed and assembled into a three-dimensional CT volume, which is then utilized to generate a three-dimensional model of the patient's "P's" airways. The three-dimensional model may be displayed on a display associated with computing device 48, or in any other suitable fashion. Using computing device 48, various views of the three-dimensional model or two-dimensional images generated from the three-dimensional model are presented. The three-dimensional model may be manipulated to facilitate identification of target 50 on the three-dimensional model or two-dimensional images, and selection of a suitable pathway through the patient's "P's" airways to access the target 50 can be made. Once selected, the pathway plan, 3D model, and images derived therefrom can be saved and exported to a navigation system for use during the navigation phase(s). One such planning software is the ILOGIC® planning suite currently sold by Medtronic. Details of such planning software are described in commonly owned and co-pending U.S. Published Patent Application No. 2014/027044 entitled "Pathway Planning System and Method" filed Mar. 15, 2013, the entire contents of which are incorporated herein by reference.

With respect to target identification, different from the currently marketed ILOGIC® software, in addition to the capability of reviewing CT images to identify calcifications representing either lesions or tumors, in accordance with the present disclosure, the CT image data, and the software applications for analyzing the CT image data are also capable of detecting and identifying hypodense areas in the CT images, as well as the vasculature, either from 3D image analysis or by incorporating angiogram, CT angiogram data, or PET/CT image analysis. These different data sets, which may be generated from multiple different image sets can either be fused, or layered, or otherwise registered together such that relevant data from each data set can be presented in a useable form enabling identification of the area to be treated (e.g., hypodense areas), the vasculature around that area to be treated, as well as the airways leading to that target. In this way, according to the present disclosure the planning software allows the clinician to identify the hypodense areas to target, the vasculature around that hypodense area to either target for sealing and coagulation, or to avoid, the adjustment of power and durations of microwave ablation settings as well as other parameters to identify how a predicted ablation zone will impact the tissue (both directly treated and distal of the treatment locations), and finally incorporate the pathway planning described above, and navigation aspects described below.

Yet a further aspect of the present disclosure is a predictive outcome application. With all the procedures described herein, there will be follow-up CT imaging and most likely pulmonary function testing. These data, particularly the CT image data and particularly contrast enhanced CT imaging or PET/CT imaging, can be collected in an effort to identify the actual outcomes associated with the treatments described herein and at a minimum determine if follow-up procedures are necessary. By comparing actual outcomes to the treatment parameters better guidelines can be given to the clinicians. More importantly the planning software (described above) can rely on this data to adjust the expected treatment zone given a wide array of factors including size of alveolus 11 treated, size of blood vessels in the treatment area, location in the lung (e.g., which bifurcation), power and duration of ablation and others. As a result, overtime the predictions in the planning software are refined to provide greater accuracy.

The aforementioned PET/CT imaging may be particularly useful in determining the effects of ablation. PET/CT imaging provides accurate and detailed results of sealing in blood vessels in an ablation zones by clearly identifying them as areas with little to no metabolic activity. Indeed, PET/CT imaging has the capability to resolve blood vessels down to the 1 mm. Such clarity is particularly useful in showing the sealing of microvasculature and the boundaries of coagulation-necrosis. In contrast traditional CT and even CT angiography may not resolve as clearly the vessel sealing in an otherwise identifiable ablation zone. Such clarity may be useful in ensuring complete treatment of the affected area.

Another aspect of the planning software described herein is the ability to propose an approach from the several described herein, including tools needed, power, duration, whether embolic are needed as well, and other parameters including susceptibility modification of the parenchyma with sterile saline or another fluid with high susceptance that are believe associated with a successful outcome. Thus, for example with reference to the slider on the user interface on whether to have a more volume reduction focus or a more blood flow shunting focus for the procedure, as the clinician slides that slider, the suggested approach, the tools needed, etc., may all change to arrive at the desired outcome with the clinician's preference in mind.

With respect to the navigation phase, a six degrees-of-freedom electromagnetic tracking system 40, e.g., similar to those disclosed U.S. patent application Ser. No. 14/753,288 to Brown et al. entitled "System and Method for Navigating within the Lung," and published PCT Application Nos. WO 00/10456 and WO 01/67035, the entire contents of each of which is incorporated herein by reference, or other suitable positioning measuring system, is utilized for performing registration of the images and the pathway and navigation, although other configurations are also contemplated. As described above, locatable guide 32 and sensor 34 are configured for insertion through an extended working channel 12 into a patient's "P's" airways (either with or without bronchoscope 30) and are selectively lockable relative to one another via a locking mechanism. Though described herein generally with respect to the use of sensor 34 being placed on the locatable guide, those of skill in the art will understand that the sensor may be placed on the EWC 12 or on instruments inserted through the EWC 12 such as a microwave ablation catheter 16 or other diagnostic and treatment modalities sized and shaped to be navigated within the lungs either with or without the EWC 12.

As shown in FIG. 7, transmitter mat 46 is positioned beneath patient "P." Transmitter mat 46 may also be arranged as a planar mounted bedside device affixed to a boom (not shown). Transmitter mat 46 generates an electromagnetic field around at least a portion of the patient "P" within which the position of a plurality of reference sensors 44 and the sensor element 34 can be determined with use of a tracking module 42. One or more of reference sensors 44 are attached to the chest of the patient "P." The six degrees of freedom coordinates of reference sensors 54 are sent to computing device 48 (which includes the appropriate software) where they are used to calculate a patient coordinate frame of reference. Registration, as detailed below, is generally performed to coordinate locations of the three-dimensional model and two-dimensional images from the planning phase with the patient's "P's" airways as observed through the bronchoscope 30, and allow for the navigation phase to be undertaken with precise knowledge of the location of the sensor 34, even in portions of the airway where the bronchoscope 30 cannot reach. Further details of such a registration technique and their implementation in luminal navigation can be found in U.S. Patent Application Pub. No. 2011/0085720 entitled "Automatic Registration Technique," the entire contents of which are incorporated herein by reference, although other suitable techniques are also contemplated.

Registration of the patient "P's" location on the transmitter mat 46 is performed by moving LG 32 through the airways of the patient "P." More specifically, data pertaining to locations of sensor element 34, while locatable guide 32 is moving through the airways, is recorded using transmitter mat 46, reference sensors 44, and tracking module 42. A shape resulting from this location data is compared to an interior geometry of passages of the three-dimensional model generated in the planning phase, and a location correlation between the shape and the three-dimensional model based on the comparison is determined, e.g., utilizing the software on computing device 48. In addition, the software identifies non-tissue space (e.g., air filled cavities) in the three-dimensional model. The software aligns, or registers, an image representing a location of sensor 34 with a the three-dimensional model and two-dimensional images generated from the three-dimension model, which are based on the recorded location data and an assumption that locatable guide 32 remains located in non-tissue space in the patient's "P's" airways. Alternatively, a manual registration technique may be employed by navigating the bronchoscope 30 with the sensor 34 to pre-specified locations in the lungs of the patient "P", and manually correlating the images from the bronchoscope to the model data of the 3D model.

Following registration of the patient "P" to the image data and pathway plan, a user interface is displayed in the navigation software which sets for the pathway that the clinician is to follow to reach the target 50. One such navigation software is the ILOGIC® navigation suite currently sold by Medtronic. Details of such navigation software are described in commonly owned and co-pending U.S. patent application Ser. No. 14/753,288 already incorporated herein by reference.

Once extended working channel 12 has been successfully navigated proximate the target 50, the locatable guide 32 may be unlocked from extended working channel 12 and removed, leaving extended working channel 12 in place as a guide channel for guiding surgical instruments including without limitation, optical systems, ultrasound probes, biopsy tools, ablation tools (i.e., microwave ablation catheter 10), laser probes, cryogenic probes, sensor probes, aspirating needles, and tools to perform lavage or susceptance modulation techniques to the target 50.

FIG. 2 depicts the result of the navigation procedure described above. In FIG. 2 the extended working channel 12 has arrived at the target 50. This placement may have been aided by the use of markers 56 and fluoroscopy or other imaging modalities as described for example in U.S. patent application Ser. No. 14/880,338, entitled "Computed Tomography Enhanced Fluoroscopic System, Device, and Method of Utilizing the Same," filed Oct. 12, 2015, the entire contents of which is incorporated herein by reference. Other imaging modalities include ultrasound, magnetic resonance imaging, computed tomography, and cone beam computed tomography, angiography, CT-angiography, PET/CT as well as others. The microwave ablation catheter 16 is depicted extending from the extended working channel 12 and engaging the target 50. Having arrived at this position, the microwave ablation catheter 16 may be energized to treat the tissue with microwave energy as described above.

As described above, a feature of the systems described herein is the use of the planning and procedure tool to identify portions of the vasculature and blood supply to a specific region, for example a hypodense area or a calcification, lesion, or tumor that has been identified as cancerous. While the foregoing has focused on using the systems described herein to treat using microwave ablation techniques, the present disclosure is not so limited. By mapping the vasculature (e.g., angiograms) and the airways as described above, a treatment plan can be created for the injection of embolic materials (either chemotherapeutic or non-chemotherapeutic) into the vasculature. Such a methodology could utilize a needle, similar to a biopsy needle to pierce the airway wall and the blood vessel into which the embolic is to be injected. The effect of the embolic materials is a highly localized embolism which results in a shunt preventing blood flow through the embolized blood vessel, and directing the blood flow to other tissues, similar to the process described above for creating a shunt using microwave ablation energy.

If the use of embolic is desired, the system may further include embolic needles, sized to fit both within the EWC 12 and designed to pierce the blood vessel walls. A wide variety of designs may be employed to enable piercing of the airway wall and blood vessel without piercing through the blood vessel. Further, there are known methods for sharps protection for such needles such than the needle or a protective catheter which is slid over the needle allows for advancement into the blood vessel without further trauma to the blood vessel. The embolic needles may include an EM sensor (as described above) to enable the tracking of the embolic needle via the EMN system 100. Such embolic needles could then be navigated within the blood vessel to reach a desired location for releasing the embolic and achieving the desired embolism in a specific blood vessel.

In further embodiments, an airway-wall piercing device may be employed to access an endobronchial tumor or other areas to be treated which is outside of the airways. In such embodiments, following navigation of the EWC 12 to a desired and removal of the locatable guide 32, or using an airway-wall piercing device equipped with an EM sensor, the airway piercing device is deployed forming a channel through the airway towards the target tissue. For example, in some scenarios it may be more expedient to exit the airway to treat a hyperinflated alveolus rather than navigate via a more complicated pathway. The air-way piercing device may include a dilator to increase the size of the opening and allow the EWC 12 to be passed through the airway. Once a channel to the area to be treated has been opened, the airway-wall piercing device may be removed in favor of one or more of the therapeutic or diagnostic tools described herein.

FIGS. 9-12 depict various aspects of a microwave ablation catheter 16. The microwave ablation catheter 16 is configured to house a microwave antenna 160 (shown in FIG. 4). Microwave ablation catheter 16 and particularly ablation catheter 160 are configured to couple to a microwave energy generator 52 (FIG. 7) that is configured to transmit microwave energy to treat target tissue, e.g., lung tissue.

Figure 9:
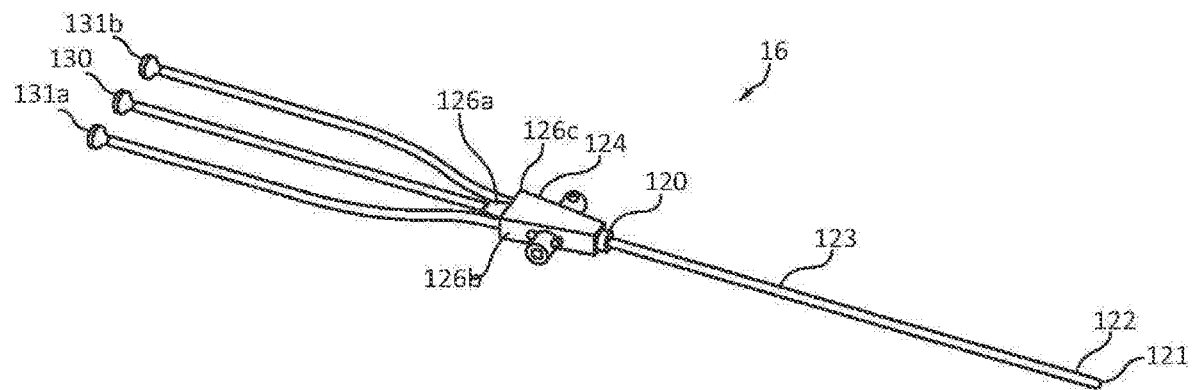
FIG. 9 is a perspective view of a microwave ablation device according to an embodiment of the instant disclosure.

The microwave ablation catheter 16 shown in FIG. 9 is configured to receive the ablation catheter 16a and to provide a pathway for a cooling medium to circulate within the microwave ablation catheter 16 and cool the microwave antenna 16a when the ablation catheter 160 is energized. As importantly as cooling, the circulation of water creates an area of homogeneous dielectric constant proximate the microwave antenna which enables efficient energy transfer and promotes the formation of consistent and spherical ablation zones. Microwave ablation catheter 16 may be formed by over molding plastic to form a generally elongated housing 123 having an outer sheath 118 (FIGS. 10A-10D) and a plurality of lumens 119a, 119b, and 119c extending from a proximal end 120 to a distal end 122 that includes a relatively pointed distal tip 121. A hub 124 receives a proximal end 120 of the housing 123 and includes ports 126a, 126b, 126c for receiving a microwave feedline 130 and inlet and outlet fluid lines 131a and 131b. Microwave feedline 130 connects either directly or indirectly to microwave generator 52. Fluid lines 131a and 131b are configured to couple either directly or indirectly to a fluid source (not shown) that provides one or more suitable cooling mediums (e.g., water, saline, air or combination thereof) to the microwave ablation antenna 16a.

The ports 126b and 126c of the microwave ablation catheter 16 are in fluid communication with corresponding lumens 119a, 119c (FIG. 10A) within sheath 118 and are configured to provide one of the aforementioned cooling mediums to the microwave antenna 16a. In an embodiment, such as the embodiment illustrated in FIG. 9, port 126b is an outflow port and provides a point of egress for the cooling medium from outflow lumen 119a and port 126c is an inflow port and provides point of ingress for the cooling medium into the inflow lumen 119c.

Figure 10A:
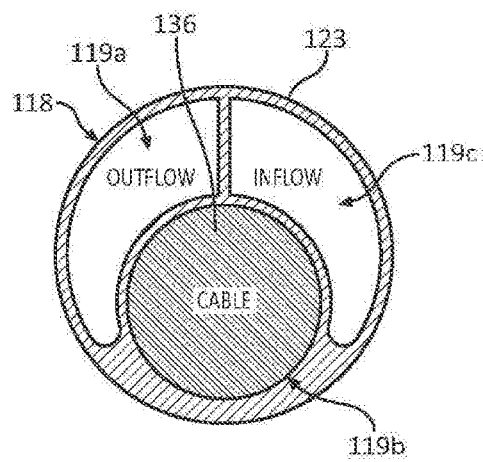
FIG. 10A is a front view of an embodiment of a lumen configuration of a microwave ablation catheter.
Figure 10C:
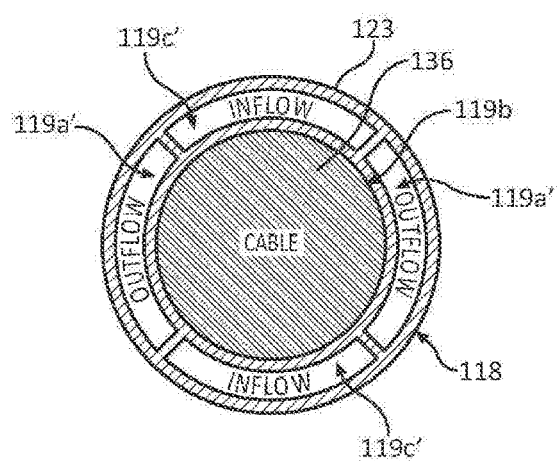
FIG. 10C is a front view of an another embodiment of a lumen configuration of a microwave ablation catheter.
Figure 10B:
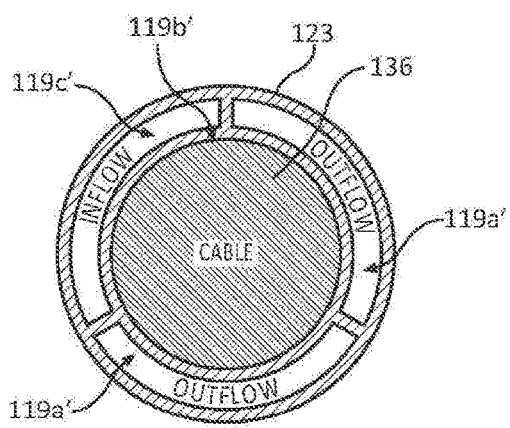
FIG. 10B is a front view of an another embodiment of a lumen configuration of a microwave ablation catheter.

FIG. 10B illustrates an alternate lumen configuration that may be utilized with the microwave ablation device catheter 16. In this embodiment, two outflow lumens 119a' and one inflow lumen 119c' are provided and are in fluid communication with the respective ports 126b, 126c. FIG. 10C illustrates an alternate lumen configuration having two outflow lumens 119a' and two inflow lumens 119c' in fluid communication with the respective ports 126b, 126c.

Figure 10D:
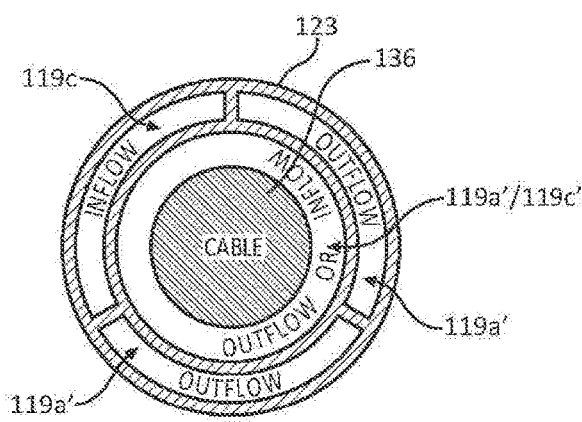
FIG. 10D is a front view of an another embodiment of a lumen configuration of a microwave ablation catheter.

FIG. 10D illustrates an alternate lumen configuration that may be utilized with the ablation device 60. In this embodiment, two outflow lumens 119a' and one inflow lumen 119c' are provided and are in fluid communication with the respective ports 126b, 126c. Additionally, the lumen supporting the coaxial microwave cable 136 is also used for either fluid inflow or outflow.

In each embodiment 10A-10D a lumen 119b is provided within the microwave ablation catheter 16 and is configured to support the microwave antenna 16a, a portion of which coaxial cable 136 is shown in each figure. In the embodiment illustrated in FIG. 4A, the outflow and inflow lumens 119a, 119c are formed above the lumen 119b. In the embodiment illustrated in FIGS. 4B and 4C, the lumen 119b is centered between the outflow lumens 119a and inflow lumens 119c to provide opposing outflow lumens 119a and opposing inflow lumens 119c around the lumen 119b. The lumen configurations illustrated in FIGS. 10A-10D provide a microwave ablation catheter 16 with the needed flexibility to move within the relatively thin conductive airways (and/or vessels) in the lungs.

The inflow and outflow lumens 119b, 119c extend a predetermined distance within the microwave ablation catheter device 16 and can function with various coolant feedback protocols (e.g., open or closed feedback protocols). In the embodiments illustrated in FIGS. 10A-10D, the inflow lumens 119c extend distally of the outflow lumens 19b to allow an adequate amount of cooling medium to circulate around the distal portion of the microwave antenna 16a.

Figure 11:
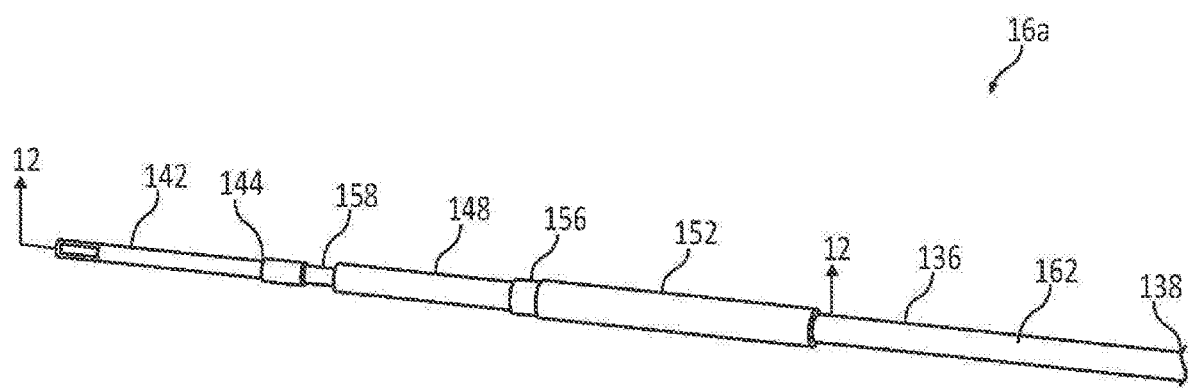
FIG. 11 is a perspective view of a microwave ablation catheter according to an embodiment of the present disclosure.
Figure 12:
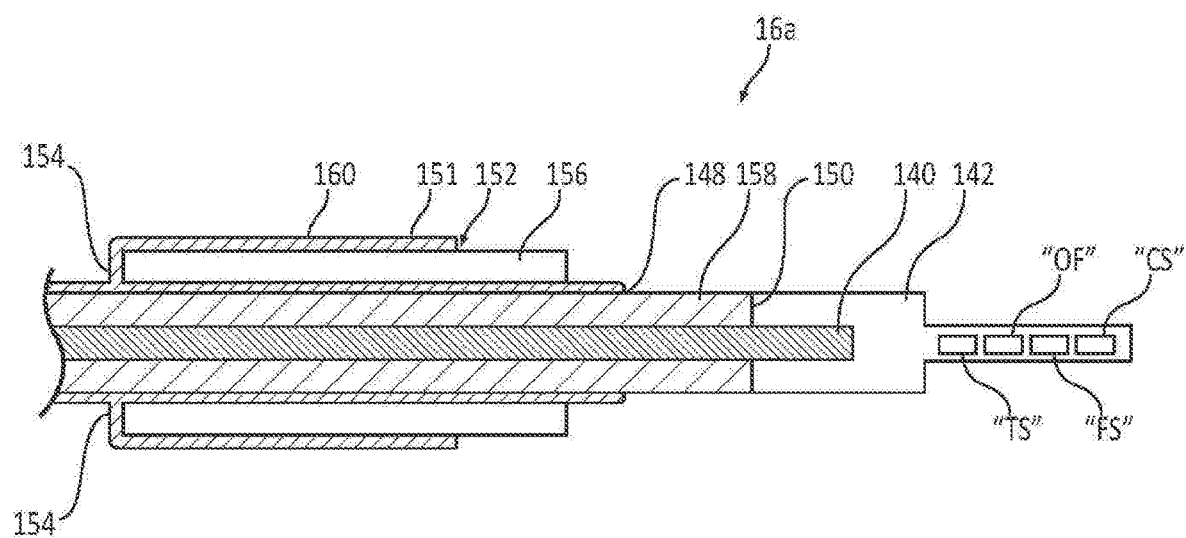
FIG. 12 is a cross-sectional view taken along line section 12-12 in FIG. 11.

Referring now to FIGS. 11 and 12, the microwave antenna 16a is illustrated. Microwave antenna 16a includes a coaxial cable 136. Coaxial cable 136 includes a proximal end 138 that couples through port 126a (shown in FIG. 9) to microwave feedline 130, and therewith to generator 52.

A distal radiating section 142 is provided at a distal end 144 of the coaxial cable 136 and is configured to receive the inner conductor 140, as best seen in FIG. 6. The distal radiating section 142 may be formed from any suitable material conductive material. In embodiments, the distal radiating section 142 may formed from ceramic or metal, e.g., copper, gold, silver, etc. The distal radiating section 142 may include any suitable configuration including but not limited to a blunt configuration, flat configuration, hemispherical configuration, pointed configuration. The distal radiating section 142 couples to the distal end 144 of the coaxial cable 136 via soldering, ultrasonic welding, adhesive, or the like. In one embodiment the distal radiating section 142 is sealed to the inner conductor 140 and a dielectric 150 to prevent fluid from directly contacting the inner conductor 140 between the inner conductor 140 and the dielectric 150. While the distal radiating section 142 is immersed in the fluid, the remainder of the inner conductor is sealed therfrom.

An outer conductor 148, which may be braided, and extends along the dielectric 150. The dielectric 150 is positioned between the inner and outer conductors 140, 148, respectively (FIG. 6). As defined herein braided means made by intertwining three or more strands, and while described as a braid, the actual construction is not so limited and may include other formations of outer conductors of coaxial cables as would be understood by those of ordinary skill in the art. One advantage of a braided configuration of the outer conductor 148 is that it provides the ablation antenna 16a with the flexibility to move within the relatively narrow luminal structures such as the airways of the lungs of a patient.

A choke or balun 152 is formed in part of a conductive layer 151 that extends along a portion of the coaxial cable 136. The conductive layer 151 may be a braided material of similar construction as the outer conductor 148 and is electrically connected to the outer conductor 148. Specifically, a portion of the outer conductor 148 is shorted (e.g., soldered, interbraided or otherwise affixed) to a proximal portion 154 of the conductive layer 151.

The choke 152 also includes an insulative layer 156, which may be formed of a polytetrafluoroethylene (PTFE). The insulative layer 156 is generally formed between the conductive material 152 and the outer conductor 148. The insulative layer 156 extends distally past a distal end of the conductive layers 151. The insulative layer 156 and its orientation extending beyond the conductive layer 151 can be adjusted during manufacture to control the overall phase shift of the balun 152 in order to better control the size and shape of the ablation zone.

The outer conductor 148 extends distally beyond the insulative layer 156. A portion of the outer conductor 148 is removed to expose the dielectric 150 of the coaxial cable 136 and form a feed gap 158. The feed gap 158 is located distally from the choke 152 and proximal of and immediately adjacent the distal radiating section 142. The feed gap 158 is located and dimensioned to achieve a specific radiation pattern for the microwave ablation antenna 16a.

The microwave ablation antenna 16a may optionally include an outer sheath 162 that extends to the proximal end 154 of the choke 152. In yet a further embodiment the sheath 162 may be a layer of PET that extends proximally along the length of the coaxial cable 136 to assist in maintaining the braided configuration of the outer conductor 148 and at least a portion of conductive layer 151. As will be appreciated by those of skill in the art, removal of the outer sheath 162 and replacing it with a thin insulative material, either along the length of the coaxial cable 136 or just at the choke 152 increases the flexibility of the antenna 16a. This added flexibility is beneficial for enabling greater ranges of movement when the microwave ablation antenna 16a is used in luminal networks having small diameters and having a branched structure of multiple sharp turns.

In embodiments, a temperature monitoring system, e.g., microwave thermometry, may be utilized with the microwave ablation antenna 16a to observe/monitor tissue temperatures in or adjacent an ablation zone. In an embodiment, for example, one or more temperature sensors "TS" may be provided on the microwave ablation antenna 16a, e.g., adjacent the distal radiating section 142 (as shown in FIG. 12) and may be configured to measure tissue temperatures in or adjacent an ablation zone. The temperature monitoring system can be, for example, a radiometer 54, a thermocouple based system, or any other tissue temperature monitoring system known in the art. The temperature monitoring system may be incorporated into or provide feedback to the generator 52 and may provide audible or visual feedback to the clinician during use of the microwave ablation antenna 16a. In embodiments, temperature sensors may be included along the coaxial cable 136, or along microwave ablation antenna 16a or along the extended working channel 12 to provide a greater array of temperature data collection points and greater detail on the temperature of the tissue following application of energy.

In at least one embodiment, the tissue temperature and/or ablation zone temperature information may be correlated to specific known ablation zone sizes or configurations that have been gathered through empirical testing and stored in one or more data look-up tables and stored in memory of the generator 52 or computing device 48 and associated with either a temperature sensing monitoring system or the radiometer 54. Data look-up tables may be accessible by a processor of the generator 52 or the radiometer 54 and accessed by the processor while the distal radiating section 142 is energized and treating target tissue. In this embodiment, the temperature sensors "TS" provide tissue temperature and/or ablation zone temperature to the microprocessor which then compares the tissue temperature and/or ablation zone temperature to the known ablation zone sizes stored in the data look-up tables. The microprocessor may then send a command signal to one or more modules of the generator 52 or the radiometer 54 or temperature sensing monitoring system to automatically adjust the microwave energy output to the distal radiating section 142. Alternatively, a manual adjustment protocol may be utilized to control the microwave energy output to the distal radiating section 142. In this embodiment, the microprocessor may be configured to provide one or more indications (e.g., visual, audio and/or tactile indications) to a user when a particular tissue temperature and/or ablation zone temperature is matched to a corresponding ablation zone diameter or configuration. In general the devices, components, and systems of the present disclosure may be optimized to produce spherical ablation zones.

While the present disclosure has been described in detail with regard to certain aspects and embodiments, though of skill in the art will recognize that alternative arrangements and components may also be employed without departing from the scope of the present disclosure.

The invention claimed is:

1. A method comprising:
  receiving image data of lungs of a patient;
  identifying one or more locations within the image data depicting symptoms of chronic obstructive pulmonary disease (COPD) by rendering coarse thresholded values of the image data as a three dimensional (3-D) model of affected areas of the lungs to distinguish enlarged alveoli from tissue;
  analyzing airways and vasculature proximate the identified one or more locations;
  planning a navigation pathway to the identified one or more locations;
  displaying the navigation pathway to aid in navigating an extended working channel to one of the identified one or more locations;
  displaying a representation of a microwave ablation catheter proximate one of the identified one or more locations for providing guidance in positioning the microwave ablation catheter;
  delivering microwave energy to the microwave ablation catheter to treat the identified one or more locations depicting symptoms of COPD;
  sensing a temperature of tissue at one of the identified one or more locations;
  comparing the sensed temperature to a predetermined temperature;
  adjusting the delivery of microwave energy to the microwave ablation catheter based on the comparison;
  placing the microwave ablation catheter proximate enlarged alveoli;
  temporarily and reversibly sealing at least one airway proximate at least one of the identified one or more locations;
  collapsing tissue in fluid communication with the sealed at least one airway; and
  inserting needle ablation probes into the tissue and applying energy to create coagulated zones.

2. The method of claim 1, further comprising placing the microwave ablation catheter proximate a region of the lungs where over production of mucus affects ventilation (V).

3. The method of claim 1, further comprising applying a vacuum to the sealed airway such that air within the alveoli is removed.

4. The method of claim 1, further comprising mechanically collapsing the tissue.

5. The method of claim 4, further comprising increasing chest cavity volume into which untreated lung tissue can expand.

6. The method of claim 1, further comprising coagulating tissue of alveoli in the collapsed state.

7. The method of claim 6, further comprising increasing a ventilation (V) of the untreated lung tissue.

8. The method of claim 1, further comprising sealing at least one pulmonary blood vessel associated with the alveoli.

9. The method of claim 8, wherein the at least one pulmonary blood vessel supplies blood to the identified one or more locations depicting symptoms of COPD.

10. The method of claim 9, further comprising forming a shunt directing blood flow away from the at least one sealed pulmonary blood vessel to untreated portions of the lungs.

11. The method of claim 10, further comprising increasing perfusion (Q) of the blood supply to untreated lung tissue.

12. A method comprising:
rendering coarse thresholded values of image data as a three dimensional (3-D) model of affected areas of a lung of a patient to distinguish enlarged alveoli from tissue to identify affected areas of the lung of the patient corresponding to one or more locations depicting symptoms of chronic obstructive pulmonary disease (COPD);
planning a navigation pathway to the one or more locations;
displaying the navigation pathway to aid in navigating a guide catheter to the identified one or more locations;
sensing a temperature of tissue at one of the identified one or more locations;
comparing the sensed temperature to a predetermined temperature;
adjusting, based on the comparison, delivery of microwave energy to a microwave ablation catheter received through the guide catheter for treating the tissue;
placing the microwave ablation catheter proximate enlarged alveoli;
temporarily and reversibly sealing at least one airway proximate at least one of the identified one or more locations;
collapsing tissue in fluid communication with the sealed at least one airway; and
inserting needle ablation probes into the tissue and applying energy to create coagulated zones.

13. The method of claim 12, further comprising displaying a representation of the microwave ablation catheter proximate one of the identified one or more locations for providing guidance in positioning the microwave ablation catheter.

14. The method according to claim 12, further comprising analyzing airways and vasculature proximate the identified one or more locations.

15. A surgical system comprising:
a microwave ablation catheter;
one or more processors; and
at least one memory coupled to the one or more processors, the at least one memory having instructions stored thereon which, when executed by the one or more processors, cause the surgical system to:
receive image data of a patient;
identify one or more locations within the image data depicting symptoms of chronic obstructive pulmonary disease (COPD) by rendering coarse thresholded values of the image data as a three dimensional (3-D) model of affected areas of lungs to distinguish enlarged alveoli from tissue;
plan a pathway to the identified one or more locations;
display a navigation pathway to aid in navigating the microwave ablation catheter to one of the identified locations;
display a representation of the microwave ablation catheter proximate one or more identified locations for providing guidance in positioning the microwave ablation catheter;
deliver microwave energy to the microwave ablation catheter to treat the one or more locations depicting symptoms of COPD;
sense a temperature of tissue at one of the identified one or more locations;
compare the sensed temperature to a predetermined temperature;
adjust the delivery of microwave energy to the microwave ablation catheter based on the comparison;
placing the microwave ablation catheter proximate enlarged alveoli;
temporarily and reversibly sealing at least one airway proximate at least one of the identified one or more locations;
collapsing tissue in fluid communication with the sealed at least one airway; and
inserting needle ablation probes into the tissue and applying energy to create coagulated zones.

* * * * *